United States Patent [19]
Westcott

[11] Patent Number: 6,120,525
[45] Date of Patent: Sep. 19, 2000

[54] SKIN TENSIONING DEVICE

[76] Inventor: Mitchell S. Westcott, 9 Half Mile Common, Westport, Conn. 06880

[21] Appl. No.: 09/353,251

[22] Filed: Jul. 14, 1999

[51] Int. Cl.[7] ..................................................... A61B 17/08
[52] U.S. Cl. ............................................................ 606/216
[58] Field of Search ................................... 606/216, 232, 606/220, 219

[56] References Cited

U.S. PATENT DOCUMENTS

| 2,752,921 | 7/1956 | Fink | ......................................... 606/216 |
| 5,127,412 | 7/1992 | Cosmetto et al. . | |

OTHER PUBLICATIONS

Closure System L.L.C., Star/Suture Tension Adjustment Reel, Brochure (approximately Jun. 1998).

*Primary Examiner*—Michael Buiz
*Assistant Examiner*—Hoa B. Trinh
*Attorney, Agent, or Firm*—Cantor Colburn LLP

[57] ABSTRACT

The present invention provides a skin tensioning device. The skin tensioning device includes an anchor member having a body portion and a pair of first suture guide slots. The anchor member is positioned at one side of a wound. A winding assembly is coupled by sutures to the anchor member. The winding assembly comprises a winder body having a first end and an opposing second end. Similar to the anchor member, the winder body includes a pair of second suture guide slots. The winder body is positioned at an opposite side of the wound. The suture is looped through the first and second suture guide slots of the anchor member and winder body, respectively, so that the suture also extends through the skin beneath each member and across the wound. The first end of the winder body includes a retaining groove which is formed in sidewalls and a bottom surface thereof. The second end of the winder body includes a beveled shoulder formed therein. The winding assembly also includes a reel having a first end and an opposing second end. A ratchet is provided at the second end and an annular retaining flange, which is received within the retaining groove of the winder body, is formed at the first end. Intermediate the first and second ends is a rail which is disposed parallel to an axis of rotation of the reel. The rail has a catch lip portion which captures the suture as the reel is cranked thereby winding the suture around the reel and drawing the anchor member and winder body toward one another and eventually brining margins of the wound into apposition for conventional suturing.

22 Claims, 9 Drawing Sheets

SKIN TENSIONING DEVICE

BACKGROUND OF THE INVENTION

1. Field of the Invention

The present invention relates to a surgical aid and more particularly relates to a device for stretching or expanding skin for the purpose of facilitating a difficult closure of large skin wounds which are routinely encountered in general surgical fields, e.g., trauma and more specialized fields such as general and reconstructive plastic surgery, orthopedic, podiatric, and chronic wounds.

2. Brief Description of the Related Art

As is traditionally known in the surgical field, when surgeons are faced with medium sized defects, the margins of which are not easily approximated, the surgeons will undercut the wound edges a few centimeters to in order to mobilize tissue for a relaxed closure. If the surgeon is faced with even larger defects which would be even more difficult to close, the surgeon may perform a wound covering skin graft by bringing in a completely detached portion of extra tissue from a distant site on the body. In this situation, the surgeon may also construct a cover for the wound in the form of a skin flap by elevating redundant, contiguous, near-by tissue and then partially detaching it, moving it, and seating it into the defect.

The ability to stretch or expand adjacent skin to generate extra tissue for wound cover is due to the fact that skin, when intermittently tensioned, will significantly elongate beyond its intrinsic limits, without damage to the physical integrity of the skin. This results because the collagen fibers, which form skin, have the ability to uncoil, align, and compact more closely together in response to a sustained, applied load. The collagen fibers thus have no power of retraction. When skin which has been stretched is anchored to a fixed point, the natural elasticity imparted by the relatively weak elastic fibers, is unable to revert the skin back to its original state.

There are three general purposes in which a skin tensioning device may be used. First, a skin tensioning device may be used to generate additional tissue for the sutured closure of surgically created skin defects in either their pre-operative or intra-operative state. Second, the device may be used to traction assist the natural contraction and non-sutured closure of open skin defects which may have been surgically operated or may have been the result of trauma or pressure. Third, the device may act as an adjustable retention suture bolster in the post-operative phase of general surgical procedures, including replacement and reconstructive surgery (e.g., hip or knee replacement surgery).

One conventional skin tensioning device of the prior art is found in U.S. Pat. No. 5,127,412 to Cosmetto et al. and is hereby incorporated by reference in its entirety. FIG. 1 shows a prior art device commercially available from the assignee hereof and is marketed under the trade name "STAR". As shown in FIG. 1, the tension set 10 includes an anchor member 12 having a body portion 14 and a pair of suture guide slots 16 formed in a bottom thereof. A winder 18 is coupled by sutures to anchor 12. Winder 18 has a body portion 20 with suture guide slots 24 formed in the bottom not unlike anchor 12. Winder 18 also includes a central reel 26 with suture anchoring guide slots 28, a ratchet 30 at one end. A driver 32 is complementary to ratchet 30 and is used to ratchet reel 26. A typical wound is sutured using tension set 10 by passing a suture 36 through one of suture guide slots 16 in body 14 of anchor member 12. Suture 36 then enters the full thickness of the skin, exits through the subcutaneous tissue and extends across the wound. It enters the subcutaneous tissue of the opposite side of the wound and is passed up and through the full thickness of the skin and then across the surface of the skin parallel to the length of the wound. Suture 36 then passes through one of suture guide slots 24 in winder body 20 and then through one of suture guide slots 28 of central reel 26. Suture 36 is then passed across and through the other of suture guide slots 28 of central reel 26 and then through the other of suture guide slots 24 in winder body 20. Suture 36 then re-enters the skin and passes the full thickness of the skin exiting through the subcutaneous tissue of the same side as winder 18 and then extends back across to the opposite side of the wound where it re-enters the subcutaneous tissue and passes up through the skin into and through the other of guide slots 16 of anchor member 12. It is then tied to the free end of suture 36 at the starting point. The externalized suture 36 on the side of the wound opposite winder 18 and reel 26 is grasped by the comb-like sidewall of anchor member 12. Thereafter, winder 18 is ratcheted by the surgeon to apply tension through sutures 36 in parallel manner across the wound, thereby stretching the skin. This skin tensioning process may take place before or during the operation while the skin extends under the gentle tension applied by tension set 10.

While the skin tensioning device of U.S. Pat, No. 5,127,412 and other prior art devices have particular utility as a skin tensioning device, the process of using this device involves a multiplicity of steps during a surgical procedure. For example, suture 36 had to be loaded into both the winder body 20 and the central reel 26. More specifically, suture 36 was passed through one of suture guide slots 24 in winder body 20 and then also had to be passed through one of suture guide slots 28 formed in central reel 26 before being looped across central reel 26 and passed through the other of suture guide slots 28 formed in central reel 26. Suture 36 was then passed through the other of guide slots 24 in winder body 20 before extending across the wound. After having loaded suture 36 in both central reel 26 and winder body 20, central reel 26 is inserted into winder body 20 to permit the ratcheting action to wind suture 36, and thereby stretch the skin. Consequently, this prior art device required the surgeon or other user to carefully couple suture 36 to central reel 26 by threading suture 36 through the pair of suture guide slots 28 in central reel 26. These steps add complexity and time to the skin tensioning process using this prior art device. In addition, because suture 36 is coupled to reel 26 through the pair of suture guide slots 28, any movement of reel 26 will accordingly cause suture 36 to be displaced. For instance, if the operator wishes to remove or reposition reel 26 in relation to winder body 20, suture 36 will also be unnecessarily pulled in this direction.

Accordingly, it would be desirable to provide a skin tensioning device which offers the utility of the prior art device; however, reduces the complexity of use and generally reduces the number of steps required by the skin tensioning process using such a device.

SUMMARY OF THE INVENTION

The present invention is directed generally to a surgical apparatus and more specifically, is directed to a skin tensioning device. The skin tensioning device includes an anchor member having a body portion and a pair of suture guide slots formed in a bottom surface thereof. Each of the pair of suture guide slots inwardly extends from one of first and second ends of the anchor member body. A winding assembly is coupled by a suture to the anchor member. The winding assembly comprises a winder body having a first end and an opposing second end. Similar to the anchor member, the winder body includes a pair of suture guide slots preferably formed in a bottom surface of the body and inwardly extending from the first and second sides thereof. The first end of the winder body includes a retaining groove which is formed in sidewalls and the bottom surface of the winder body. The second end of the winder body includes a beveled shoulder formed therein and extending generally outward from the bottom surface of the winder body.

The winding assembly also includes a reel having a first end and an opposing second end. A ratchet is provided at the second end and an annular retaining flange which is received within the retaining groove of the winder body is formed at the first end. Intermediate the first and second ends is a rail which is disposed parallel to an axis of rotation of the reel and is generally perpendicular to the ratchet and annular retaining flange. The rail has a catch lip portion which captures the suture as the reel is cranked thereby winding the suture around the reel. Drive openings are preferably formed in each of first and second ends of the reel. In a preferred and exemplary embodiment, the drive openings are hexagonal in shape and receive a complementary end of a crank which is used to crank the reel disposed within the winder body. It will be appreciated that other cranking mechanism may be used in the present invention. For example the reel may include a spring disposed therein so that the winding of the reel is driven by a wound-up or coiled spring force. During the cranking action, the ratchet gears of the reel engages the complementary beveled shoulder of the winder body to permit the cranking action in a direction the crank is being rotated. As is known in the art, the beveled shoulder prevents the reel from being cranked in direction against the gears of the ratchet and therefore the beveled shoulder acts as a stop. A stabilizer is also preferably provided for holding the winder body during the cranking action of the reel. The stabilizer comprises a knob having a pair of prongs extending therefrom. The prongs are received in stabilizing slots formed in outer surfaces of the winder body so that the stabilizer securely holds the winding assembly during the winding action. Alternatively, the stabilizer may be formed as part of the molded winder body, wherein on side of the stabilizer is hinged to permit the other side of the stabilizer to be lifted to permit access to the winder body for the reel so that the reel may be either inserted or removed from the winder body.

A typical wound is sutured using the skin tensioning device of the present invention by first laying the suture in a mattress configuration across the wound. The free ends of the suture are tied to complete the mattress configuration. After laying the mattress configuration, the suture on both sides of the wound is positioned so that the suture passes through the suture guide slots formed in the anchor member disposed on one side of the wound and the suture guide slots formed in the winder body disposed on the other side of the wound. Accordingly, the suture is first laid in the mattress configuration across the wound prior to the suture being coupled to the anchor member and the winder body by disposing the suture in intended receiving suture guide slots of each.

A typical wound may also be sutured using the skin tensioning device of the present invention in a slightly different manner than that previously described by first passing the suture through one of the suture guide slots in the body of the anchor member. The suture then enters the full thickness of the skin, exits through the subcutaneous tissue and extends across the wound. It enters the subcutaneous tissue of the opposite side of the wound and is passed up and through the full thickness of the skin and then across the surface of the skin parallel to the length of the wound. The suture then passes through one of the suture guide slots in the winder body and then extends across the bottom of the winder body to the other suture guide slot. The suture then passes through this other suture guide slot in the winder body and then re-enters the skin and passes the full thickness of the skin exiting through the subcutaneous tissue of the same side as the winder body and then extends back across to the opposite side of the wound where it reenters the subcutaneous tissue and passes up through the skin into and through the other of the guide slots of the anchor member. It is then tied to the free end of the suture at the starting point. This type of suture configuration is commonly referred to as a "mattress" configuration.

Once the sutured has been tied and is disposed within the suture guide slots in both the anchor member and the winder body, the reel is inserted into the winder body by aligning and inserting the annular flange of the reel within the retaining groove of the winder body. The ratchet portion of the reel is likewise inserted into the second end of the winder body so that the ratchet gears engage the beveled shoulder of the winder body. The externalized suture disposed across the bottom of the winding body between the pair of suture guide slots is grasped by the catch lip portion of the rail as the reel is cranked by the drive crank in a direction in which a plurality of the ratchet gears engage the beveled shoulder of the winder body to produce an interlocking cranking rotation of the reel. As the reel is cranked and a portion of the suture has been grasped by the catch lip, the suture continuously and automatically winds around the reel between the annular flange and ratchet portions as the reel rotates. This ratcheting by the surgeon applies tension to the skin through the sutures in a parallel manner across the wound, thereby stretching the skin. As the reel is continuously cranked, the lateral skin sketches as margins approach one another. This skin tensioning process may take place before or during the operation while the skin extends under the gentle tension applied by the device of the present invention.

The above-discussed and other features and advantages of the present invention will be appreciated by and understood by those skilled in the art from the following detailed description and drawings.

BRIEF DESCRIPTION OF THE DRAWINGS

Referring now to the drawings wherein like elements are numbered alike in the several FIGURES.

DETAILED DESCRIPTION OF THE PREFERRED EMBODIMENT

Referring to FIGS. 2–9, an exemplary and preferred skin tensioning device is illustrated and generally indicated at 100. Skin tensioning device 100 comprises a surgical device which can be easily attached to the skin in order to facilitate the difficult closure of medium and large skin wounds. Utilizing the established biomechanical and visco-elastic principles of relaxation and mechanical creep, skin tensioning device 100 is able to mobilize otherwise unavailable skin for difficult surgical closures. In addition, skin tensioning device 100 may also be used as a retention suture. It is further within the scope of the present invention that skin tensioning device 100 may also be applied to non-difficult surgical closures in order to reduce the necessity for wound edge undercutting. Because multiple devices 100 may be simultaneously attached, the length of the closure is not a limiting factor. The design of skin tensioning device 100 renders it extremely durable, reusable, mechanically simple, low in profile, and minimally traumatic to the skin during use. The device 100 held by the suture allows the patient to ambulate with minimal risk of accidental reopening of the wound. Skin tensioning device 100 also includes a quick release feature which permits the operator the option of stretchrelaxation cycling. Although skin tensioning device 100 is very effective as a pre-operative and intra-operative tissue expander, it is within the scope of the present invention that skin tensioning device 100 may also serve post-operatively as a retention suture bolster which is capable of adjusting to tension fluctuations caused by edema or abdominal distention. Skin tensioning device 100 may also serve as a traction device which facilitates the contraction of open granulating defects for which no sutured closure is planned. Typical clinical applications include but are not limited to wide linear excisions, alopecia reduction surgery, tissue flap expansion, laparoptomy retention suturing, and traction-assisted closured of open defects due to trauma, Moh's surgery and decubiti. In order to fully understand skin tensioning device 100 of the present invention, skin tensioning device 100 will be described in great detail and the method of the use of skin tensioning device 100 will be described. The methods of use generally breaks down into intra-operative usage, pre-operative usage, and a usage for non-adjustable post-operative retention.

Figure 2:
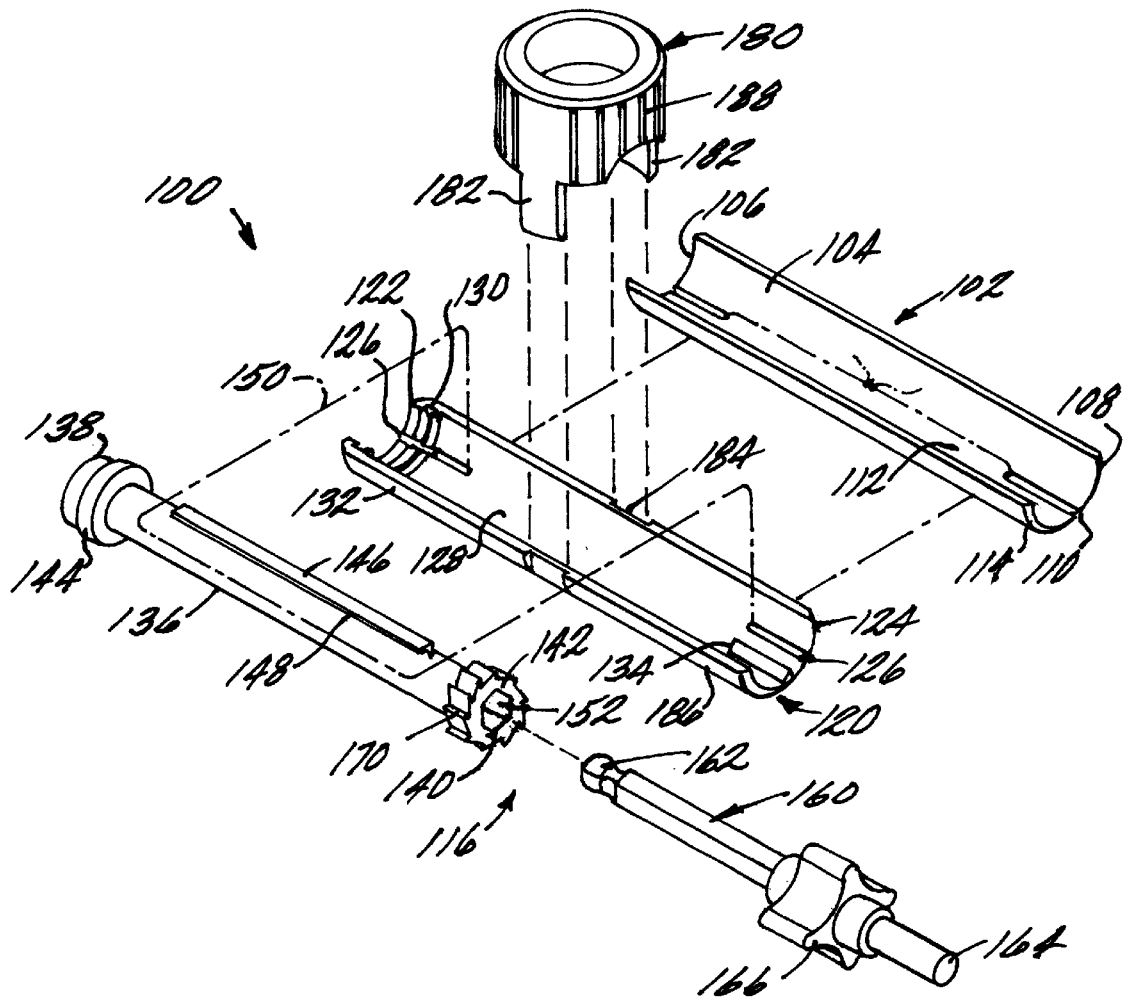
FIG. 2 is an exploded perspective view of a skin tensioning device in accordance with the present invention.

As best shown in FIG. 2, skin tensioning device 100 includes an anchor member 102 having a body portion 104 having a first end 106 and an opposing second end 108. A pair of linear first suture guide slots 110 are formed in a bottom surface 112 of body 104 so that each of the pair of first suture guide slots 110 inwardly extends from one of first and second ends 106 and 108, respectively, of anchor member body 104. In a preferred and exemplary embodiment, body 104 is generally semicircular in nature and has opposing sidewalls 114 integral with bottom surface 112 which is generally arcuate in shape.

A winding assembly 116 is coupled by suture 150 to anchor member 102. Preferably suture 150 comprises a monofilament suture. Winding assembly 116 includes a winder body 120 having a first end 122 and an opposing second end 124. Similar to anchor member 102, winder body 120 includes a pair of linear second suture guide slots 126 preferably formed in a bottom surface 128 of winder body 120, wherein the pair of second suture guide slots 126 inwardly extend from first and second ends 122 and 124, respectively, of bottom surface 128. First end 122 of winder body 120 includes a retaining groove 130 which is formed in sidewalls 132 and bottom surface 128 of winder body 120. Second end 124 of winder body 120 includes a beveled shoulder 134 formed therein and generally outwardly extend from sidewall 132 and bottom surface 128 of winder body 120.

Winding assembly 116 also includes a reel 136 having a first end 138 and an opposing second end 140. A ratchet 142 is provided at second end 140 and an annular retaining flange 144, which is received within retaining groove 130 of winder body 120, is formed at first end 138. Intermediate first and second ends 138 and 140 is a rail 146 which is disposed parallel to an axis of rotation of reel 136 and is generally perpendicular to ratchet 142 and annular retaining flange 144. Rail 146 has a catch lip portion 148 which captures suture 150 as reel 136 is cranked thereby winding suture 150 around reel 136. Drive openings 152 are preferably formed in each of first and second ends 138 and 140, respectively, of reel 136. In a preferred and exemplary embodiment, drive openings 152 are hexagonal in shape and receive a complementary drive end 154 of a crank 160 which is used to crank reel 136 disposed within winder body 120. During the cranking action, ratchet 142 of reel 136 engages the complementary beveled shoulder 134 of winder body 120 to cause a cranking action in a direction crank 160 is being rotated. As is known in the art, beveled shoulder 134 prevents reel 136 from being cranked in direction against gears 170 of ratchet 142 and therefore beveled shoulder 134 acts as a stop. The preferred method of cranking reel 136 is to insert crank 160 in drive opening 152 formed in second end 140 which is the end including ratchet 142 and then rotating crank 160 in the ratcheting direction.

A stabilizer 180 is also preferably provided to hold winder body 120 during the cranking action of reel 136. Stabilizer 180 comprises a knob having a pair of prongs 182 extending therefrom. Prongs 182 are received in stabilizing slots 184 formed in an outer surface 186 of winder body 120 so that stabilizer 180 securely holds winding assembly 116 during the winding action. In the exemplary embodiment, stabilizer 180 is generally circular in shape and includes outer ribs 188 to aid in the handling and holding of stabilizer 180 during its use as described hereinafter. Stabilizing slots 184 are formed in outer surface 186 of winder body 120 intermediate and preferably centrally disposed between annular retaining flange 144 and ratchet 142.

Figure 16:
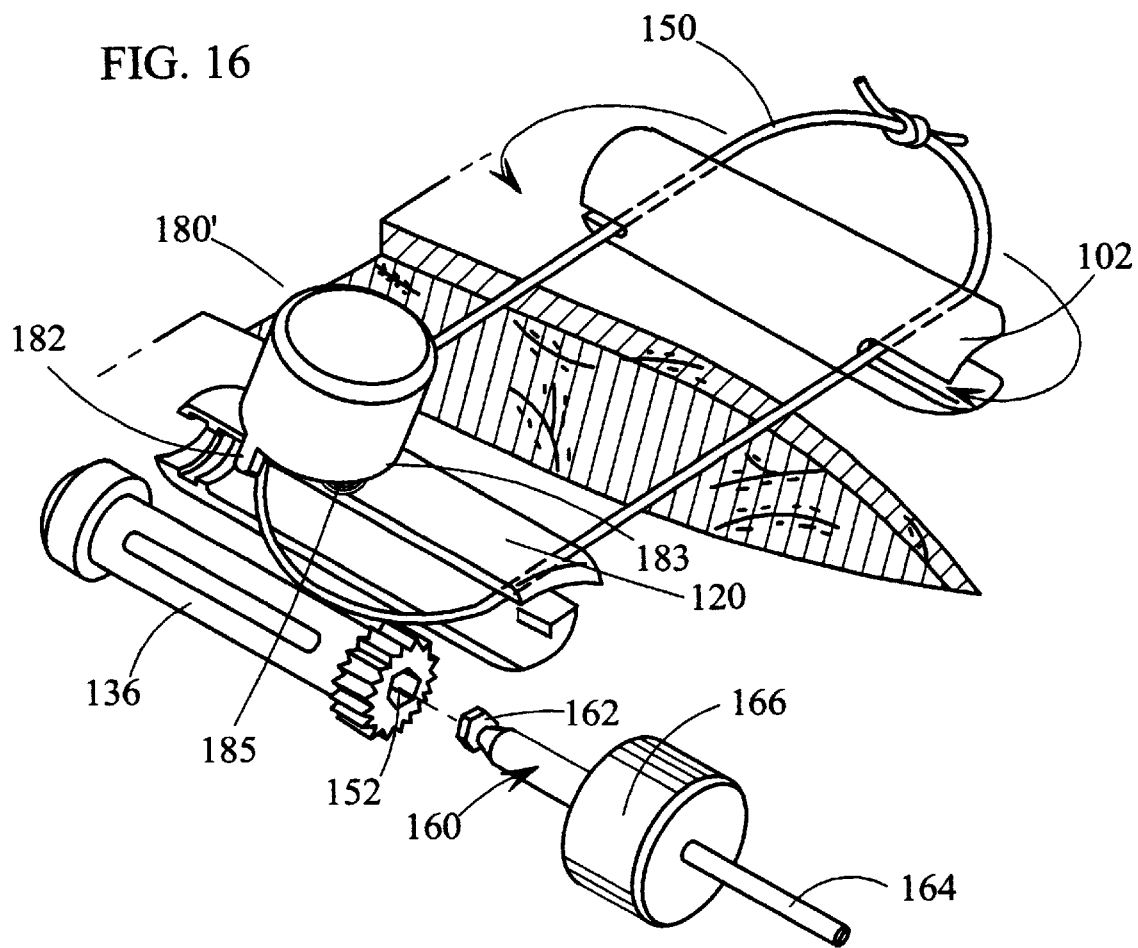
FIG. 16 illustrates an exemplary embodiment wherein the winder body and stabilizer of the skin tensioning device of the present invention are securely coupled to one another.

Alternatively, as shown in FIG. 16, stabilizer 180' may be securely coupled to winder body 120 by having one end 183 of stabilizer 180 securely attached to winder body 120 in a hinged manner. In other words, one of prongs 182 is eliminated and instead is replaced by a hinge 185 which permits stabilizer 180' to be hinged open at one end 183 causing oppositely disposed prong 182 to disengage the complementary stabilizing slot 184 formed in winder body 120. By moving stabilizer 180' so that it opens at hinge 185, access to winder body 120 is created so that reel 136 may be inserted or removed from winder body 120. In this embodiment, hinge 185 may be integrally formed with stabilizer 180' and winder body 120 and hinge 185 comprises conventional hinge mechanisms that permit stabilizer 180' to be lifted sufficiently to create access to the inner cavity of winder body 120. Accordingly, hinge 185 must permit stabilizer 180' to be hingedly lifted so that reel 136 may be easily removed from or inserted into winder body 120.

The exemplary and preferred crank 160 includes a hexagonal drive head 162 which is complimentary in shape to drive openings 152 so that drive head 162 intimately engages one of drive openings 152. Opposite drive head 162 is an end 164 which in the exemplary embodiment is generally circular in cross section. Intermediate drive head 162 and end 164 is a holder 166 which aids the operator in grasping, holding, and rotating crank 160. In the exemplary embodiment, holder 166 two sets of opposing sides, each side having a concave surface which is intended to receive an operator's finger. It will be appreciated that other cranking devices may be used to cause reel 136 to wind suture 150 therearound. For example, reel 136 may be spring loaded so that reel 136 is driven by a wind up or coiled spring force. In other words, the spring contained within reel 136 is tightened to build-up the coiled spring force and then the built-up spring force is released causing reel 136 to uncoil and drive rotation of reel 136 which results in the reel 136 winding suture 150.

In accordance with the present invention, skin tensioning device 100 is preferably formed of a plastic material which permits skin tensioning device 100 to be disposable and easily reusable, if it is desired. Although it is within the scope of the invention that other materials may be used to form part or all of skin tensioning device 100.

Figure 3:
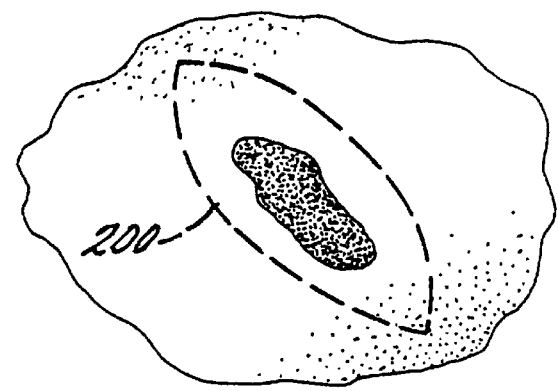
FIG. 3 is a proposed surgical margins sketching drawn on the skin prior to an operation.
Figure 4:
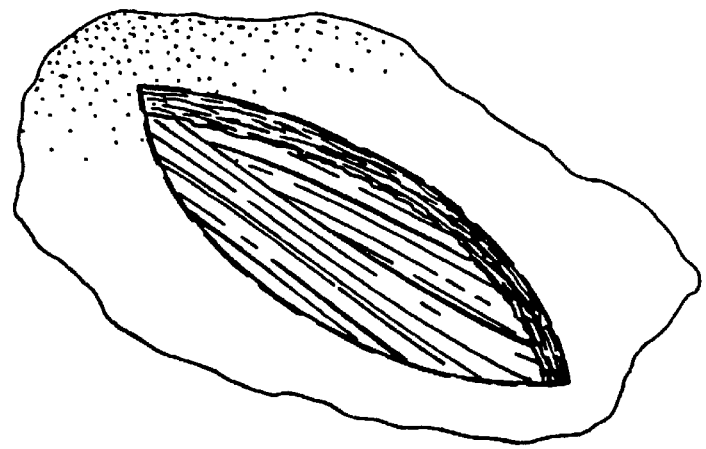
FIG. 4 discloses the full thickness of tumor along the presults from excision of a tumor along the proposed surgical margins of FIG. 3.
Figure 5:
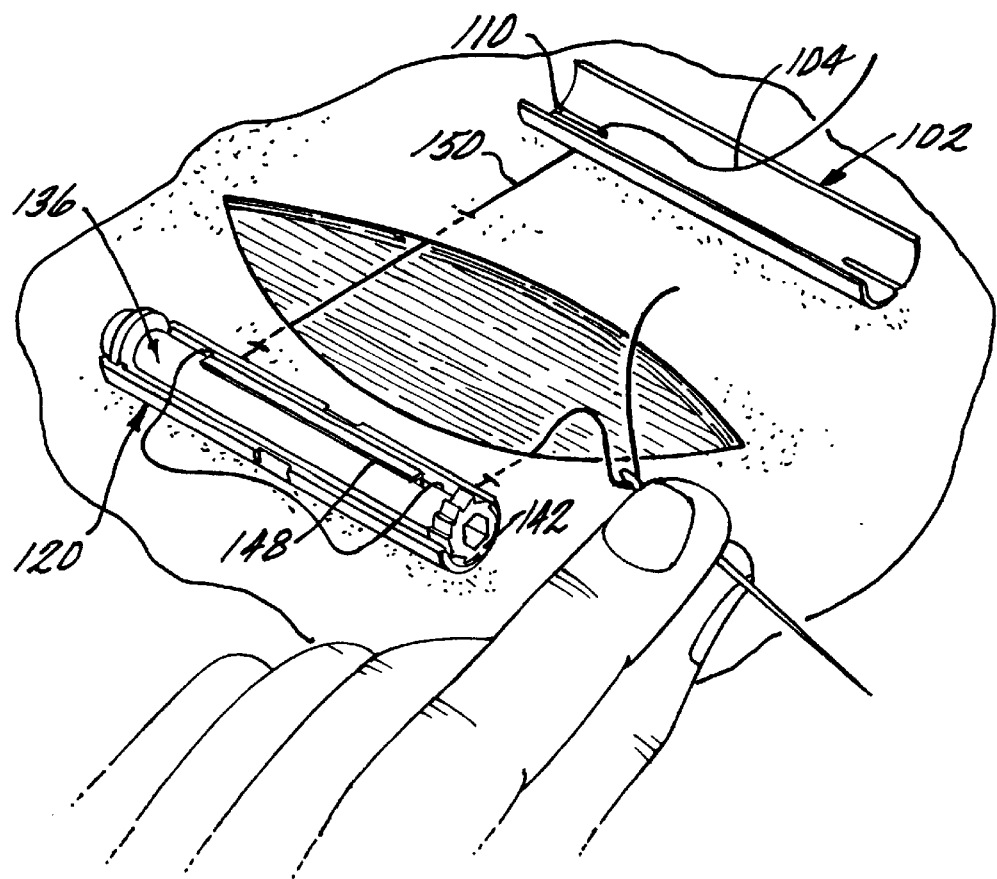
FIG. 5 shows the skin tensioning device of the present invention attached to the margins of an open defect at the time of surgery and illustrating the hand of the surgeon, needle, and suture as applied.
Figure 6:
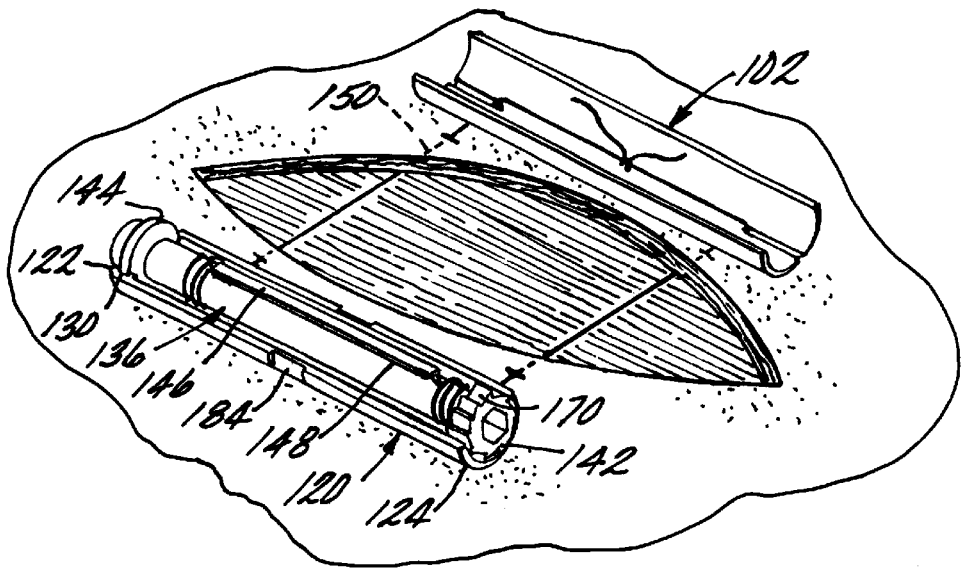
FIG. 6 shows the skin tensioning device of the present invention fully attached with the suture knot tied.

Now turning to FIGS. 3–9 which illustrate the intraoperative use of skin tensioning device 100. In the intraoperative use of skin tensioning device 100, proposed surgical margins 200 are drawn on the skin, as shown in FIG. 3. Thereafter, a tumor or the like, is excised along proposed surgical margins 200 and following this procedure, the wound appears as shown in FIG. 4. As shown in FIG. 5, the wound is sutured using skin tensioning device 100 of the present invention by passing suture 150 through one of first suture guide slots 110 in body 104 of anchor member 102. Suture 150 then enters the full thickness of the skin, exits through the subcutaneous tissue and extends across the wound. It enters the subcutaneous tissue of the opposite side of the wound and is passed up and through the full thickness of the skin and then across the surface of the skin parallel to the length of the wound. Suture 150 then passes through one of second suture guide slots 126 (not shown in FIG. 4) in winder body 120 and then extends across bottom 128 of winder body 120 to the other of second suture guide slots 126. Suture 150 then passes through this other of second suture guide slots 126 in winder body 120 and then re-enters the skin and passes the full thickness of the skin exiting through the subcutaneous tissue of the same side as winder body 120 and then extends back across to the opposite side of the wound where it re-enters the subcutaneous tissue and passes up through the skin into and through the other of first guide slots 110 of anchor member 102. It is then tied to the free end of suture 150 at the starting point. FIG. 6 illustrates suture 150 fully attached with the suture knot tied. Accordingly, it is preferred that suture 150 be tied at the side where anchor member 102 is disposed and not at the side where winder body 120 is disposed. It being understood that a tied mattress type suture configuration may be laid across the wound and then suture 150 may be inserted and fitted into first suture guide slots 110 of anchor member 102 and second suture guide slots 126 of winder body 120.

Figure 1:
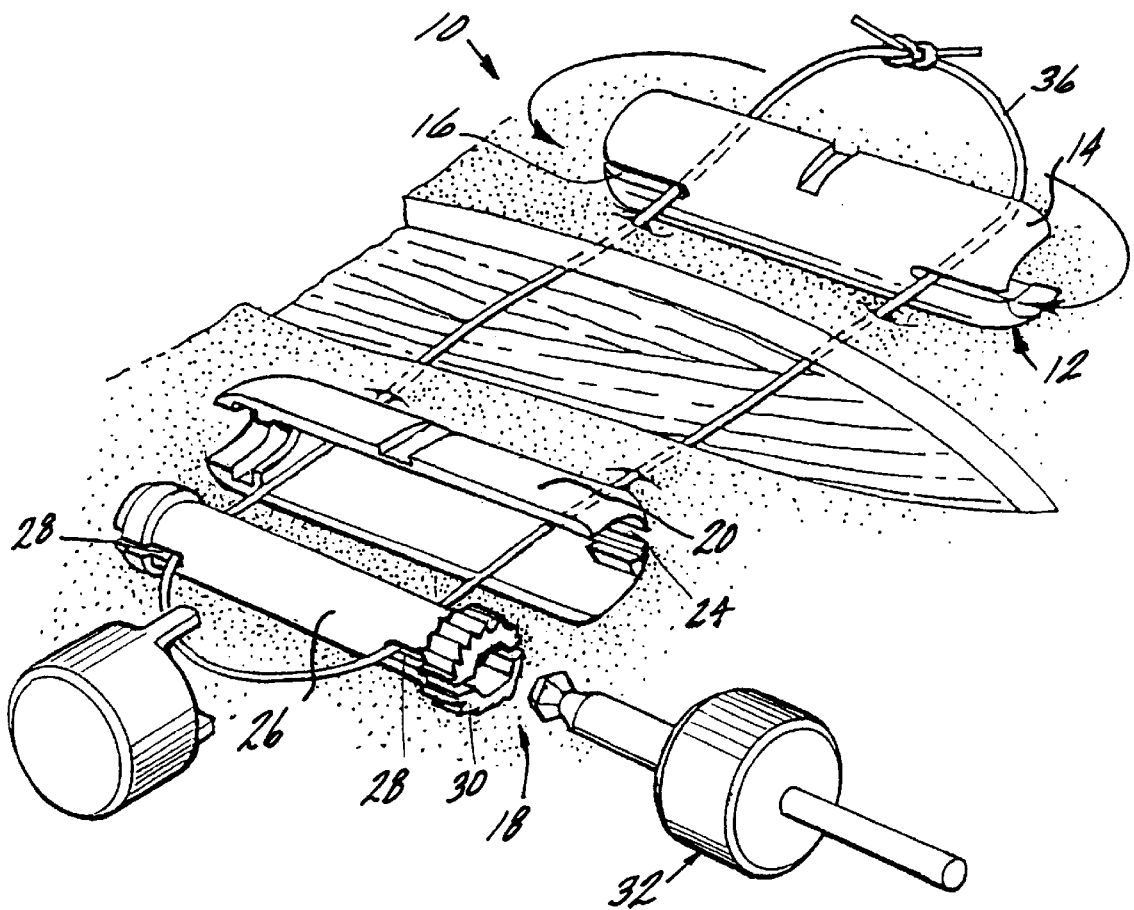
FIG. 1 is an exploded perspective view of a tension set of the prior art.
Figure 7:
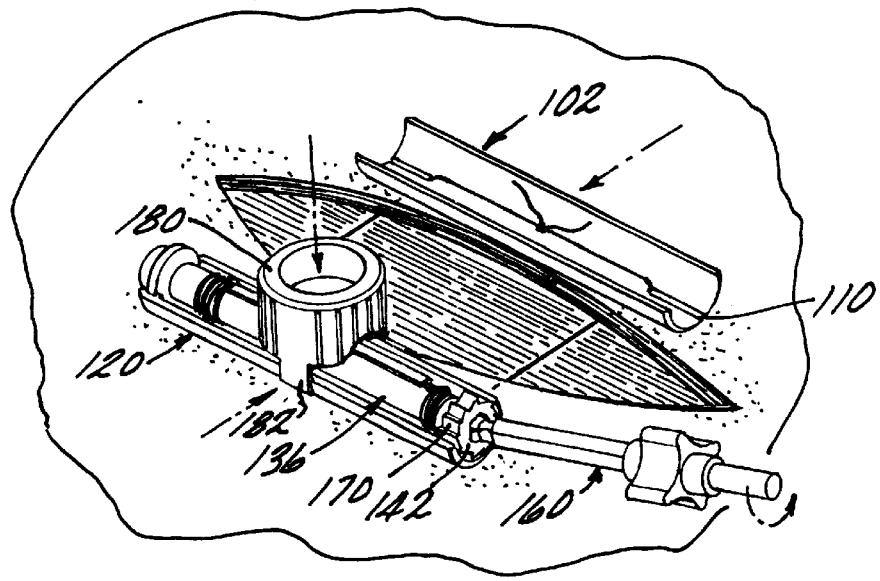
FIG. 7 illustrates lateral skin stretches as margins approach one another.
Figure 8:
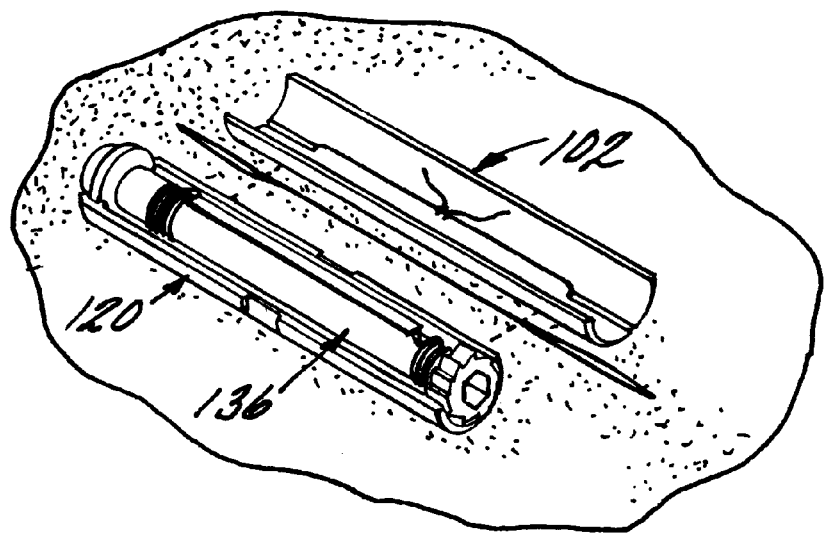
FIG. 8 illustrates the margins eventually meeting one another as a result of the skin elongating and the slack being picked up by further cranking of the skin tensioning device.
Figure 9:
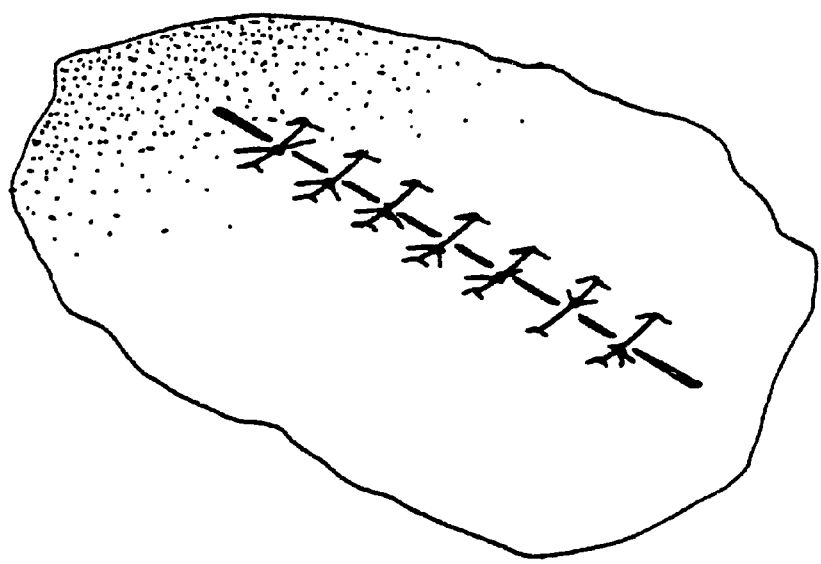
FIG. 9 illustrates the wound after the present skin tensioning device has been removed with the relaxed edges as traditionally sutured.

Once the sutured has been tied and is disposed within the first and second suture guide slots 110 and 126, respectively, in both anchor member 102 and winder body 120, reel 136 is inserted into winder body 120 by aligning and inserting annular retaining flange 144 of reel 136 within retaining groove 130 at first end 122 of winder body 120. Ratchet portion 142 of reel 136 is inserted into second end 124 of winder body 120 so that ratchet 142 engages beveled shoulder 134 of winder body 120. The externalized suture 150 disposed across bottom 128 of winding body 120 between the pair of second suture guide slots 126 is grasped by catch lip portion 148 of rail 146 as reel 136 is cranked by drive crank 160 (FIG. 1) in a direction in which ratchet gears 170 engage beveled shoulder 134 of winder body 120 to produce an interlocking cranking rotation of reel 136. As reel 136 is cranked and a portion of suture 150 has been grasped by the catch lip 148, suture 150 continuously and automatically winds around reel 136 between the annular retaining flange 130 and ratchet 140 as reel 136 rotates. This ratcheting by the surgeon applies tension through sutures 150 in a parallel manner across the wound, thereby stretching the skin. Stabilizer 180 (FIG. 7) and more specifically, prongs 182 engage stabilizing slots 184 so that stabilizer 180 securely holds winder body 120 during the winding action. Sequentially thereafter, as shown in FIG. 7, the lateral skin stretches as the margins approach one another. Optionally, tension may be released by raising ratchet 142 upward so that ratchet gears 170 off beveled shoulder 134 (not shown) in a manner which is also useful in cycling. As is shown in FIG. 8, as the skin elongates, slack may be picked up by further cranking and the margins eventually meet each other. Finally, as shown in FIG. 9, skin tensioning device 100 is removed and the defect with relaxed edges is traditionally sutured as shown. In special situation, such as the elongation of a very small or delicate skin flap, the non-active member (anchor member 102) may be omitted. The suture loop 150 would be attached directly to the leading edge of the skin flap and then directed towards and passed through the active member (winder body 120) which would be stationed at a more distant site.

Figure 10:
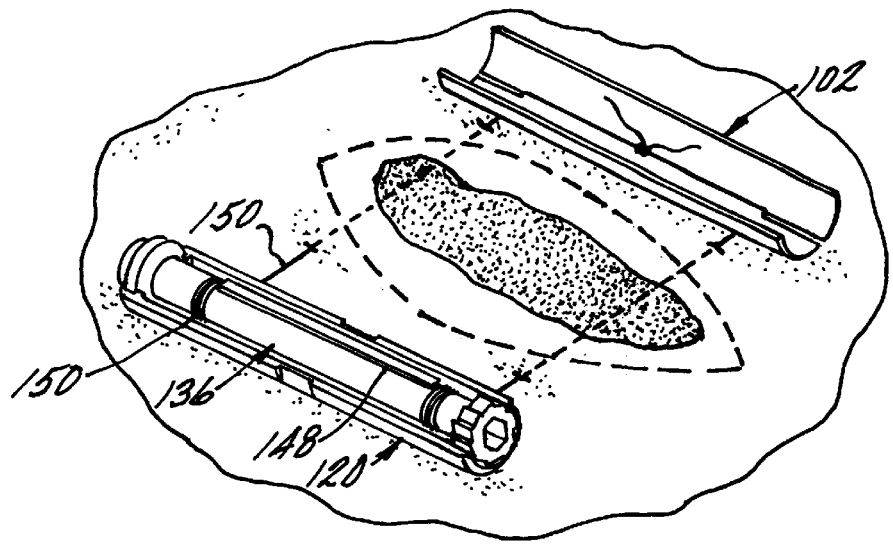
FIG. 10 illustrates the skin tensioning device sutured to the skin, before surgery, in such a manner as to fold the tumor upwardly.
Figure 11:
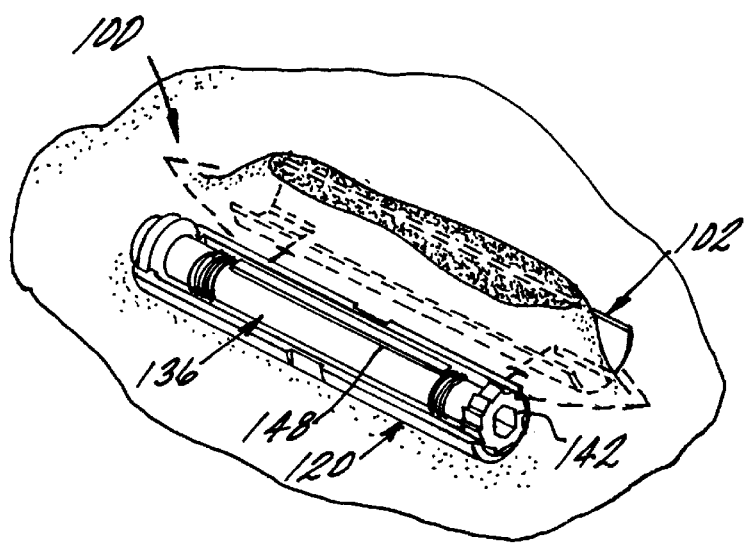
FIG. 11 is a sequential illustration to FIG. 10 in which the skin tensioning device is tightened and lateral areas of the skin are stretched.

It is also within the scope of the present invention that skin tensioning device 100 may be used pre-operatively. The pre-operative use of skin tensioning device 100 begins with drawing the proposed margins 200 on the skin as is shown in FIG. 3. Next, anchor member 102 and winder body 120 are sutured to the skin, before surgery, as shown in FIG. 10, so that a tumor, may be folded upwardly. Thereafter, as shown in FIG. 11, skin tensioning device 100 is tightened by cranking reel 136 with crank 160 (FIG. 1) so that suture 150 is initially caught by catch lip 148 and as reel 136 is cranked, suture 150 winds around reel 136 resulting in anchor member 102 and the skin being drawn inward toward reel 136 and winder body 120. Upon the completion of cranking reel 136, the skin is all raised and the tumor is folded upwardly for removal. Then, skin tensioning device 100 is removed and the tumor is excised along the proposed margins. FIG. 4 illustrates the full thickness defect which results from the removal of the tumor with the edges being prestretched. Thereafter, the relaxed defect, as shown in FIG. 9, is traditionally sutured.

Figure 12:
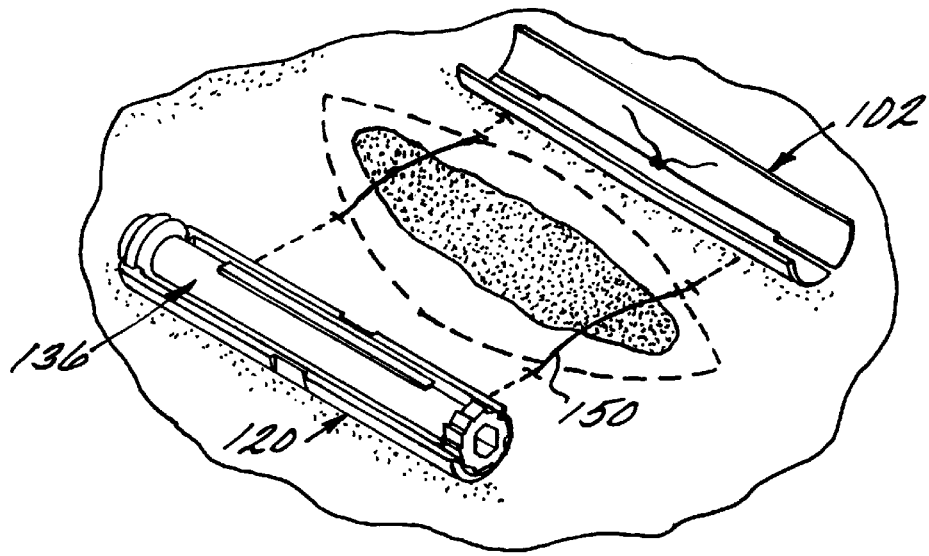
FIG. 12 illustrates the skin tensioning device sutured to the skin, before surgery, in such a manner as to fold the tumor beneath the skin tensioning device.
Figure 13:
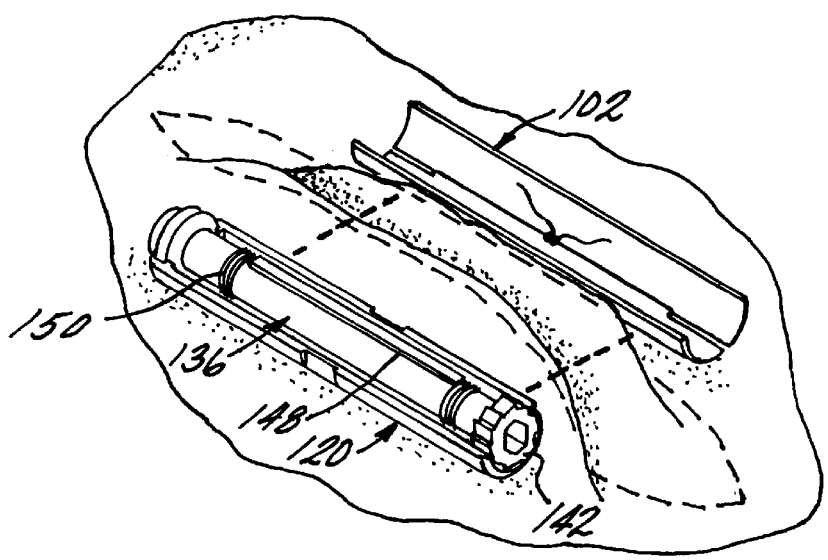
FIG. 13 illustrates the skin tensioning device tightened with the stretching of the lateral areas.

An alternative pre-operative use of skin tensioning device 100 is shown with reference to FIGS. 3, 5, 9 and 12–13. Here again the proposed surgical margins are drawn on the skin as shown in FIG. 3. Thereafter, skin tensioning device 100 is sutured to the skin as shown in FIG. 12 prior to surgery, but in a manner so as to fold the tumor beneath skin tensioning device 100. Subsequently, as shown in FIG. 13, skin tensioning device 100 is tightened and lateral area are stretched. Thereafter, upon conclusion of the stretching, the pre-operative use of skin tensioning device proceeds and concludes as described with reference to FIGS. 5 and 9.

Figure 14:
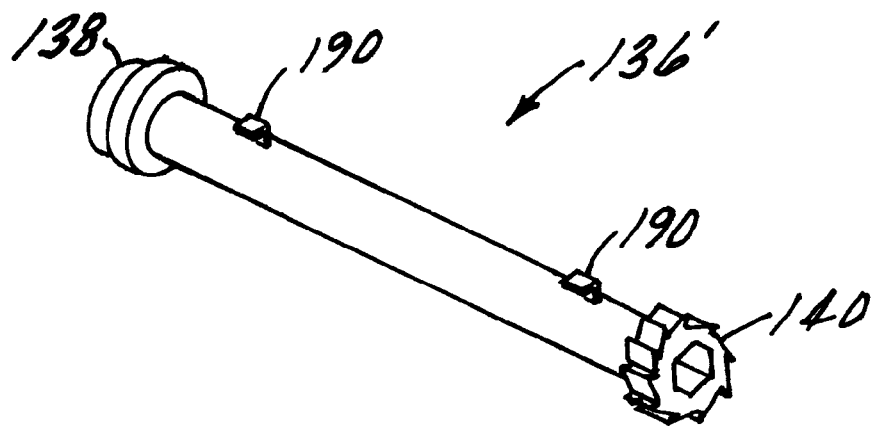
FIG. 14 illustrates a reel having a second embodiment in accordance with the present invention.
Figure 15:
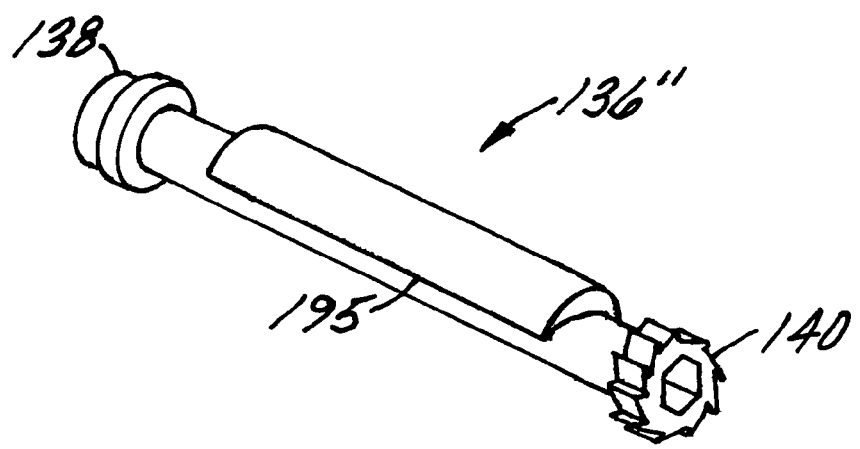
FIG. 15 illustrates a reel having a third embodiment in accordance with the present invention.

FIG. 14 illustrates a reel having a second embodiment and is generally shown at 136'. In this embodiment, reel 136' includes at least one and preferably at least two spaced hooks 190 along the outer surface of reel 136'. Hooks 190 are designed to act similar to rail 146 and catch lip 148 in that hooks 190 act to catch and pick-up suture 150 as reel 136' is cranked. In the exemplary embodiment shown, hooks 190 are disposed proximate ends 138 and 140 of reel 136'. FIG. 15 illustrates yet another embodiment of a reel which is generally indicated at 136". In this embodiment, reel 136" includes a notch 195 formed within reel 136" and generally extending along a portion of the length of reel 136". Notch 195 acts as a catch and pick-up mechanism for winding suture 150 around reel 136" as reel 136" is cranked.

It being understood that the present invention has a wide spectrum of applicability in a variety of medical fields and is not limited to the foregoing description which is merely exemplary in nature. For example, it is within the scope of the present invention and is intended that the device 100 of the present invention may be used in veterinary sciences and therefore is used as a device for tensioning the skin of not only a human but also for an animal, such as a horse.

While preferred embodiments have been shown and described, various modifications and substitutions may be made thereto without departing from the spirit and scope of this invention. Accordingly, it is understood that the present invention has been described by way of illustrations and not limitation.

What is claimed is:

1. A skin tensioning device including:
   an anchor member having a first end and a second end and a pair of first suture guide slots formed therein for receiving a suture;
   a winder body having a first end and a second end and a pair of second suture guide slots, the winder body including a retaining groove formed at the first end and a beveled shoulder at the second end, the second suture guide slots for receiving the suture;
   a reel having an annular retaining flange at a first end, a ratchet at a second end, and a rail intermediate the first and second ends of the real; the annular retaining flange being received in the retaining groove of the winder body to securely couple the two together, the ratchet engaging the beveled shoulder to permit a ratchet action when the reel is rotated within the winder body, the reel having at least one drive opening formed in one of the first and second ends; and
   a drive crank for rotating the reel within the winder body.

2. The skin tensioning device of claim 1, further including:
   a stabilizer having a body with a pair of prongs extending outwardly from one end, the pair of prongs being received within stabilizing slots formed in an outer surface of the winder body intermediate the first and second ends, the body extending above and across the reel when the prongs are located within the stabilizing slots, wherein the stabilizer securely holds the winder body during cranking of the reel.

3. The skin tensioning device of claim 1, wherein the anchor member and winder body comprise semicircular shells.

4. The skin tensioning device of claim 1, wherein the first suture guide slots comprise a pair of slots inwardly extending from the first and second sides of the anchor member, the second suture guide slots comprising a pair of slots inwardly extending from the first and second sides of the winder body.

5. The skin tensioning device of claim 1, wherein the rail of the reel includes a catch lip for catching the suture as the reel is rotated within the winder body so that the suture is wound around the reel as the reel is rotated within the winder body.

6. The skin tensioning device of claim 1, wherein the anchor member is positioned at one side of a wound resting on a surface of the skin and the winder body is positioned at an opposite side of the wound resting on the skin, one end of a loop of the suture extending through the first suture guide slots of the anchor member, the other end of the loop extending through the second suture guide slots of the winder body, whereby the suture loop extends across the wound.

7. The skin tensioning device of claim 1, wherein the crank includes a drive head being received within a drive opening formed in one of first and second ends of the reel.

8. The skin tensioning device of claim 7, wherein the drive head and drive opening are hexagonal in shape.

9. The skin tensioning device of claim 5, wherein the rail and catch lip are integrally formed and generally comprise an L shaped member, a top potion being the catch lip.

10. The skin tensioning device of claim 1, wherein the ratchet includes ratchet gears which are complementary to the beveled shoulder formed in the winder body, the ratchet gears engaging the beveled shoulder during rotation of the reel.

11. The skin tensioning device of claim 1, wherein the pair of first suture guide slots are formed in a bottom surface of the anchor member and are linearly aligned with one another and the pair of second suture guide slots are formed in a bottom surface of the winder body and are linearly aligned with one another.

12. The skin tensioning device of claim 4, wherein the first suture guide slot at the second end of winder body is parallel to the beveled shoulder which extends inwardly from the second end and is generally located on a bottom surface of the winder body.

13. The skin tensioning device of claim 1, further comprising:
   a stabilizer including a body having a first end and a second end, the first side including a prong extending outwardly from the first end, the prong being received within a stabilizing slot formed in an outer surface of the winder body intermediate the first and second ends of the winder body, the second end of the stabilizer including a hinge which hingedly attaches the second end of the stabilizer to the winder body and permits the stabilizer to move between a hinged position and an engaged position, wherein in the hinged position, the reel is freely removable from the winder body and in the engaged position, the body extends above and across the reel.

14. A skin tensioning device including:

an anchor member having a first end and a second end and a pair of first suture guide slots formed therein for receiving a suture;

a winder body having a first end and a second end and a pair of second suture guide slots, the winder body including a retaining groove formed at the first end and a beveled shoulder at the second end, the second suture guide slots for receiving the suture;

a reel having an annular retaining flange at a first end, a ratchet at a second end, the annular retaining flange being received in the retaining groove of the winder body to securely couple the two together, the ratchet engaging the beveled shoulder to permit a ratchet action when the reel is rotated within the winder body, the reel having at least one drive opening formed in one of the first and second ends, means on the reel for catching and winding the suture around the body of the reel as the reel is rotated; and a drive crank for rotating the reel within the winder body.

15. The skin tensioning device of claim 14, wherein the means for catching and winding the suture around the reel comprise at least one hook disposed on the reel and extending therefrom so that the suture is caught by the hook as the reel is rotated and the continued rotation of the reel causes the suture to be continuously wound around the reel.

16. The skin tensioning device of claim 14, wherein the means for catching and winding the suture around the reel comprise a notch formed within the body of the reel, the notch extending a portion of the length of the reel so that the suture is caught in the notch as the reel is rotated and the continued rotation of the reel causes the suture to be continuously wound around the reel.

17. A method of skin tensioning, stretching, or closing a wound, comprising:

preparing a wound on the skin that provides opposed skin margins;

positioning an anchor member at one side of the wound resting on the surface of the skin;

positioning a winder body at the opposite side of the wound resting on the surface of the skin;

suturing through each of the anchor member and the winder body and then through the skin beneath the anchor member and the winder body using one continuous loop of suture material;

inserting a reel within the winder body, the reel having a rail intermediate first and second ends of the real, the rail extending outwardly from an outer surface of the reel; and rotating the reel within the winder body so that the rail of the reel catches the suture and further rotation of the reel causes the suture to be wound around the reel intermediate the first and second ends, the winding of the suture causing the winder body and anchor member to be drawn toward each other to eventually bring the margins of the wound into apposition for conventional suturing.

18. The method of claim 17, wherein the anchor member has first and second ends and a pair of first suture guide slots, the pair of first suture guide slots extending inwardly from the first and second ends, the winder body having first and second ends and a pair of second suture guide slots, the pair of second suture guide slots extending inwardly from the first and second ends of the winder body, the suture looping through the first suture guide slots at the one side of the wound and through the second suture guide slots at the opposite side of the wound.

19. The method of claim 17, wherein the insertion of the reel within the winder body, comprises:

inserting an annular retaining flange formed at the first end of the reel into a retaining groove formed in a first end of the winder body; and engaging a ratchet portion of the reel at a second end thereof with a beveled shoulder formed in the winder body.

20. The method of claim 19, wherein the rotation of the reel comprises:

inserting a drive crank into a drive opening formed in the reel;

rotating the reel in a first direction so that ratchet gears engage the beveled shoulder and the reel rotates in a ratchet like manner and the annular retaining flange rotates within the retaining groove of the winder body.

21. The method of claim 20, wherein the rail includes a catch lip which catches the suture loop extending within the winder body so that rotation of the reel causes the catch lip to pick up and wind the suture loop around the reel.

22. The method of claim 20, further comprising:

stabilizing the winder body during the rotation of the reel by securely coupling a stabilizer with the winder body, the stabilizer including a pair of prongs outwardly extending from a body, the pair of prongs being received within complementary stabilizing slots formed within an outer surface of the winder body, the stabilizer body extending above and across the reel during the rotation thereof.

* * * * *